United States Patent [19]

Buyniski et al.

[11] 4,277,605

[45] Jul. 7, 1981

[54] CHEMICAL COMPOUNDS

[75] Inventors: Joseph P. Buyniski, Syracuse, N.Y.; John W. Hooper, Pierrefonds; Gary M. F. Lim, Candiac, both of Canada

[73] Assignee: Bristol-Myers Company, New York, N.Y.

[21] Appl. No.: 128,329

[22] Filed: Mar. 7, 1980

[51] Int. Cl.$^3$ .................. C07D 221/28; A61K 31/485
[52] U.S. Cl. .................................... 546/74; 424/260
[58] Field of Search ........................................ 546/74

[56] References Cited

U.S. PATENT DOCUMENTS

| 3,256,286 | 6/1966 | Sawa et al. | 546/74 |
| 3,285,922 | 11/1966 | Gates | 546/74 |
| 3,654,280 | 4/1972 | Sawa et al. | 546/74 |
| 3,853,889 | 12/1974 | Monkovic et al. | 424/260 X |
| 3,959,290 | 5/1976 | Monkovic et al. | 424/260 X |
| 4,016,167 | 4/1977 | Montzka et al. | 424/260 X |
| 4,017,497 | 4/1977 | Lim et al. | 546/74 |
| 4,154,932 | 5/1979 | Montzka et al. | 546/63 |

OTHER PUBLICATIONS

Sawa et al., Tetrahedron, vol. 24, pp. 261–266 (1968).
Goodman et al., eds., The Pharmacological Basis of Therapeutics, 5th Ed., The MacMillan Co., (1975), pp. 263, 266.
Gates et al., J. Med. Chem., 7, pp. 127–131 (1964).

Primary Examiner—Donald G. Daus
Assistant Examiner—Diana G. Rivers
Attorney, Agent, or Firm—Richard R. Lloyd

[57] ABSTRACT

3-Hydroxy-7-oxomorphinans and 3-hydroxy-7-oxoisomorphinans, optionally substituted on the 17-nitrogen atom, are potent, orally active antidiarrheal agents.

12 Claims, 1 Drawing Figure

FIGURE 1
EFFECT OF ACUTE ORAL DOSES OF COMPOUND d,ℓ-Ib(l), DIPHENOXYLATE AND MORPHINE ON BODY WEIGHT LOSS INDUCED BY MORPHINE WITHDRAWAL IN MORPHINE-DEPENDENT RATS
(10 mg/kg b.i.d.)

CHEMICAL COMPOUNDS

SUMMARY OF THE INVENTION

3-Hydroxy-7-oxomorphinans and 3-hydroxy-7-oxoisomorphinans of the formula

I wherein $R^1$ is hydrogen, (lower)alkyl, cyclopropylmethyl, cyclobutylmethyl, propargyl, allyl or 3,3-dimethylallyl, and nontoxic pharmaceutically acceptable acid addition salts thereof, are potent, orally active antidiarrheal agents with little or no liability or produce physical dependence.

BACKGROUND AND PRIOR ART

Narcotics such as opium, morphine and codeine have long been used in the symptomatic treatment of diarrhea. However, these drugs have the undesirable property of producing psychological and physical dependence, as well as other central nervous system opiate effects. Many attempts have been made to separate the antidiarrheal activity from the central nervous system effects in synthetic opiates or opiate-like compounds, and some success has been achieved in this effort.

(A) Diphenoxylate, having the structure is a known, potent antidiarrheal agent; see, for example, *The Pharmacological Basis of Therapeutics*, 5th Edition, Goodman and Gilman, eds., Pages 263 and 266, The MacMillan Company (1975). Diphenoxylate has a lowered potential to produce physical dependence because it is a highly insoluble compound, even in its salt forms, and therefore is difficult to abuse parenterally. However, abuse potential is not entirely lacking, since high oral doses (40–60 mg) produce typical opioid effects; e.g., euphoria, suppression or morphine abstinence, and a morphine-like physical dependence after chronic administration.

(B) U.S. Pat. No. 3,853,889 discloses substituted 8-oxamorphinans and 8-oxaisomorphinans having the formula wherein $R^1$ is H, (lower)alkyl, (lower)alkenyl, in which $R^6$ is H or $CH_3$; $R^2$ is H, (lower)alkyl, (lower)alkanoyl, cinnamoyl, and R³ is H or (lower)alkyl; and pharmaceutically acceptable acid addition salts thereof. The compounds are stated to be analgetic agents, narcotic antagonists or intermediates in the preparation of such agents. U.S. Pat. No. 3,959,290, a continuation-in-part of the above-identified patent, has a substantially identical disclosure.

(C) U.S. Pat. No. 4,016,167 discloses substituted 6,8-dioxamorphinans and 6,8-dioxaisomorphinans having the formula wherein R¹ is H, (lower)alkyl, (lower)alkenyl, in which R⁶ is H or CH₃; R² is H, (lower)alkyl, (lower)alkanoyl, cinnamoyl, R³ is H or (lower)alkyl; and R⁴ and R⁵ are alike or different and each is H, (lower)alkyl or trifluoromethyl, or when taken together R⁴ and R⁵ are a carbonyl function or a spiroalkyl group of 3 to 7 carbon atoms; and pharmaceutically acceptable acid addition salts thereof. The compounds are stated to possess analgetic agonist-/antagonist activity or to be useful intermediates. Other prior art is cited in columns 1-4 of this patent.

(D) U.S. Pat. No. 4,154,932 discloses 6-oxamorphinans of the formula wherein R¹ is hydrogen, (lower)alkyl, cyclopropylmethyl, cyclobutylmethyl, allyl, 3,3-dimethylallyl, —CH₂C≡CR³, in which R³ is hydrogen or methyl, and R² is hydrogen, (lower)alkyl, (lower)alkanoyl or nicotinoyl, and non-toxic pharmaceutically acceptable salts thereof. The compounds are stated to have analgetic, narcotic antagonist, antitussive and/or ADH inhibitory activity.

(E) J. Med. Chem., 7, 127–131 (1964) discloses the l-isomers of the morphinans of the formula wherein R¹ is cyclopropylmethyl, cyclobutylmethyl or (1-phenylcyclopropyl)methyl and R² is hydrogen, and 1-isomorphinans of the above structure wherein (a) R¹ is hydrogen, methyl, cyclopropylmethyl or cyano and R² is methyl, and (b) R¹ is methyl or cyclopropylmethyl and R² is hydrogen, and salts thereof. The compounds are stated to be analgesics and/or morphine antagonists.

(F) U.S. Pat. No. 3,285,922 discloses morphinans and isomorphinans of the formula wherein R is hydrogen or methyl and Y is cyclopropyl or cyclobutyl, and their optical isomers, and acid addition salts thereof. The compounds are stated to be useful as analgetics and narcotic antagonists.

COMPLETE DISCLOSURE

This application relates to antidiarrheal agents. More particularly, this application relates to 3-hydroxy-7-oxomorphinans and 3-hydroxy-7-oxoisomorphinans of the formula wherein R¹ is hydrogen, (lower)alkyl, cyclopropylmethyl, cyclobutylmethyl, propargly, allyl or 3,3-dimethylallyl, and nontoxic pharmaceutically acceptable acid addition salts thereof, which are potent, orally active antidiarrheal agents with little or no liability to produce physical dependence.

The opiates have long been known as the most effective and prompt-acting nonspecific antidiarrheal agents. Opium is probably the oldest drug on record; the Ebers papyrus, dating from about 1500 B.C., includes prescriptions containing opium. The ancient Chinese utilized opium for the control of dysenteries long before the spread of the opium habit throughout China in the latter part of the eighteenth century. In more modern times, the use of opiates such as opium, morphine and codeine for the control of diarrhea has been limited by their potential for abuse and resulting addiction. The search for potent antidiarrheal agents with little or no potential for abuse has met with some success, but there remains a need for new, potent, non-addicting antidiarrheal agents.

It was therefore an object of the present invention to find novel, potent antidiarrheal agents with little or no potential for producing physical dependence and with little or none of the usual central nervous system effects caused by the opiate-like compounds. It was a further object of this invention to develop methods for the synthesis of such compounds which would not be dependent upon opium alkaloids as starting materials. These objects have been met by the provision of the compounds of Formula I and by their total synthesis from the known compounds 3-methoxy-N-ethoxycarbonyl-7-oxo-$\Delta^{8,14}$-morphinan or 7,7-ethylenedioxy-14-hydroxy-3-methoxyisomorphian.

The compounds of Formula I have the basic morphinan nucleus and are numbered and represented by the following plane formula:

There are three asymmetric carbon atoms in the morphinan molecule (carbons 9, 13 and 14), which result in only two diastereoisomeric racemates (four optical isomers) because the iminoethano system attached to carbons 9 and 13 is geometrically constrained to a cis-1,3-diaxial fusion.

The present invention includes both the morphinans (14β-hydrogen) and the isomorphinans (14α-hydrogen), either as their diastereoisomeric and/or d,l (racemic) mixtures, or as their resolved optical isomers. The d- and l-isomers of the morphinans or isomorphinans may be separated and isolated by fractional crystallization of the diastereoisomeric salts formed by the reaction of the racemic mixture of the morphinan or isomorphinan with, for instance, d- or l-tartaric acid, D-(+)-α-bromocamphorsulfonic acid or dibenzoyl-d-tartaric acid. Alternatively, one may obtain the desired d- or l-form of a compound of Formula I by resolving and utilizing the pure d- or l-form of either the starting material or an intermediate in the synthesis of the compounds of Formula I. The morphinans are the preferred series of compounds and the l-isomers [(—)-isomers] are the preferred optical isomers.

In a preferred embodiment of this invention, the compounds have the structure of Formula I in which R¹ is hydrogen, (lower)alkyl, cyclopropylmethyl or cyclobutylmethyl.

In a more preferred embodiment of this invention, the compounds are morphinans of Formula I in which R¹ is hydrogen or (lower)alkyl.

In a still more preferred embodiment of this invention, the compound is a morphinan of Formula I in which R¹ is methyl, and most preferably the (—)-isomer thereof.

The compounds of this invention may be prepared by serveral multiple-step procedures as outlined in the following reaction schemes. In these reaction schemes, the isomorphinan series of compounds (including intermediates) are designated "a" while the morphinan series of compounds (including intermediates]are designated "b."

Reaction Scheme 1 shows the preparation of compounds of Formula I in which R¹ is methyl [Ia(1) and Ib(1)], utilizing 3-methoxy-N-ethoxycarbonyl-7-oxo-$\Delta^{8,14}$-morphinan (II) as starting material. The preparation of this starting material is described in U.S. Pat. No. 4,017,497 (see Example 38 thereof).

Reaction Scheme 2 shows the preparation of compounds of Formula I in which R¹ is methyl [Ia(1) and Ib(1)] by two alternative routes, each utilizing 7,7-ethylenedioxy-14-hydroxy-3-methoxy-N-methylisomorphinan (VIIa) as starting material. The preparation of this starting material is described in U.S. Pat. No. 4,017,497 (see Example 6 thereof).

Reaction Scheme 3 shows the preferred method of preparation of compounds of Formula I in which R[1] is (lower)alkyl other than methyl, or is cyclopropylmethyl or cyclobutylmethyl [Ia(2) and Ib(2)], utilizing Compound VIIa as starting material. Thus, to prepare a compound of Formula I in which R[1] is n-propyl by Reaction Scheme 3, one would utilize in the first reaction step the acid chloride in which R[2] was ethyl. In Reaction Scheme 3, the abbreviation "Ts" represents the "tosyl" or p-toluenesulfonyl moiety.

Reaction Scheme 4 shows a method of preparing any of the compounds of Formula I, utilizing Compound VIIa as starting material. In this procedure, a compound of Formula I in which R[1] is hydrogen is first prepared, and that intermediate (XVIIIa or XVIIIb) is alkylated with the desired alkyl group. Reaction Scheme 4 illustrates the preparation of compounds of Formula I in which R[1] is allyl [Ia(3) and Ib(3)], but it will be appreciated that use of the appropriate alkylating agent in place of allyl bromide will produce any of the compounds of Formula I.

-continued

Reaction Scheme 1

Reaction Scheme 2

Reaction Scheme 3

Reaction Scheme 3

XIVa —Same sequence of steps as from XIVb→ Ia(2)

Reaction Scheme 4

It will be appreciated by those skilled in the art that the compounds of Formula I may also be prepared by other variations which are combinations of the above Reaction Schemes. Thus, Example 9 shows a variation in which the ethoxycarbonyl moiety is removed from Compound IVb (from Reaction Scheme 1) to produce 7,7-ethylenedioxy-3-methoxymorphinan (XIXb). That compound is then N-acylated with cyclopropane carboxylic acid chloride to produce Compound XIIIb (in which $R^2$ is cyclopropyl), and the latter compound is subsequently reacted according to Reaction Scheme 3 to produce Compound Ib(2) (in which $R^2$ is cyclopropyl). Example 10 shows a similar reaction to produce the corresponding isomorphinan.

Although Reaction Schemes 1-4 list specific reagents for such steps as acylation, reduction of the acyl group, alkylation, conversion of an alkoxy group to a hydroxyl group, etc., those skilled in the art will appreciate that there are various alternative procedures for performing each of these steps.

In Reaction Scheme 3, the acylation of Compound VIIa (the first step of the two-step reaction converting VIIIa to XI) may be accomplished with any acylating agent known in the art to be suitable for acylating a secondary amine. Thus, Compound VIIa may be acylated with at least an equimolar amount of an acylating agent of the formula in which X is OH, Cl, Br or I, and $R^2$ is (lower)alkyl, cyclopropyl, cyclobutyl, ethynyl, ethenyl or 2,2-dimethylethenyl, in an inert organic solvent, in the presence of at least an equimolar amount of an appropriate base. When the acylation is conducted with the free acid (X is OH), the reaction preferably is conducted in the presence of at least an equimolar amount of a carbodiimide.

Suitable inert organic solvents for use in the acylation step are well-known to those skilled in the art, and include methylene chloride, chloroform, dichloroethane, tetrachloromethane, benzene, toluene, ether, ethyl acetate, xylene, tetrahydrofuran, dioxane, dimethylformamide, dimethylacetamide and the like.

Appropriate bases for use in the acylation step include inorganic bases such as NaOH, KOH, $K_2CO_3$, $Na_2CO_3$, $KHCO_3$, $NaHCO_3$ and the like, and those tertiary amines commonly employed as a proton acceptor in acylation reactions. Such amines are tri(lower)alkylamines; e.g., trimethylamine, triethylamine, pyridine, dimethylaniline, N-methylpiperidine and the like.

The reduction of the carbonyl group of Compound XIIIa or XIIIb to produce Compound XIVa or XIVb, respectively, may be accomplished by use of a reducing agent such as lithium aluminum hydride, aluminum hydride, diborane or sodium bis(2-methoxyethoxy)aluminum hydride, in an inert organic solvent such as diethyl ether, dioxane, tetrahydrofuran, benzene, xylene, toluene or the like.

In Reaction Scheme 4, the alkylation of Compound XVIIIa or XVIIIb to produce a compound of Formula Ia or Ib, respectively, may be accomplished by utilizing at least an equimolar amount of an alkylating agent of the formula $R^1$—Y, in which Y is Cl, Br or I, in an inert organic solvent in the presence of at least an equimolar amount of an appropriate base. The inert organic solvents and appropriate bases useful in the alkylation step include those described above for the acylation step. Additional solvents useful in the alkylation step are (lower)alkanols such as methanol, ethanol, n-propanol, isopropanol and the like.

The cleavage of the ether linkage in any of the above Reaction Schemes (conversion of methoxy to hydroxy), such as the conversion of Compound XVIIa or XVIIb to Compound XVIIIa or XVIIIb, respectively, may be accomplished by the use of such reagents as sodium thiomethoxide, sodium thioethoxide, lithium thiomethoxide, lithium thioethoxide, hydrobromic acid, boron tribromide or pyridine hydrochloride. Suitable solvents for this cleavage reaction will be known to those skilled in the art. Thus, when using sodium thiomethoxide, lithium thiomethoxide, sodium thioethoxide or lithium thioethoxide, suitable solvents include dimethylformamide, toluene, xylene, hexamethylphosphoramide and the like. When using boron tribromide, suitable solvents include methylene chloride, ether, chloroform, dichloroethane, carbon tetrachloride and the like. Hydrobromic acid may be utilized, for example in aqueous solution (e.g. 48%) or in acetic acid solution. Pyridine hydrochloride may conveniently be used in excess, where it serves as its own solvent.

Acylations, alkylations, reduction of ketone groups and cleavage of ether linkages such as set forth above are described for related compounds in U.S. Pat. Nos. 3,803,150, 3,819,635, 3,853,889, 4,016,167, 4,017,497 and 4,154,932, the disclosures of which are incorporated herein by reference.

For the purpose of this disclosure and the appended claims, the term (lower)alkyl is defined as a straight or branched chain alkyl group containing from 1 to 6 carbon atoms, e.g. methyl, propyl, isobutyl, etc. The term "nontoxic pharmaceutically acceptable salt" is defined as a salt of a compound of this invention with any of the inorganic or organic acids which are commonly used to produce nontoxic salts of medicinal agents containing amine functions. Illustrative examples would be those salts formed by mixing the compounds of Formula I with hydrochloric, sulfuric, nitric, phosphoric, phosphorous, hydrobromic, maleic, malic, ascorbic, citric, tartaric, pamoic, lauric, stearic, palmitic, oleic, myristic, lauryl sulfuric, naphthalenesulfonic, linoleic or linolenic acid, or the like.

Compounds of Formula I in which $R^1$ is hydrogen (Compounds XVIIIa and XVIIIb) are also intermediates (via Reaction Scheme 4) for other compounds of Formula I wherein $R^1$ is other than hydrogen. It will be appreciated that, when utilized as an intermediate, the acid addition salts of Compounds XVIIIa and XVIIIb need not be "nontoxic pharmaceutically acceptable" salts.

Salts of the free bases may be prepared by conventional means, e.g. by addition of the appropriate acid to a solution of the free base in ethanol, 1-propanol, 2-propanol, acetone-methanol, acetone-ethanol or the like. Salts of the compounds may be converted to the free base by treatment of the salt with dilute $K_2CO_3$ or $Na_2CO_3$ and extraction with $CH_2Cl_2$. The extract is dried with $MgSO_4$, $Na_2SO_4$ or $K_2CO_3$ and then concentrated to give the free base (generally in 100% yield).

For therapeutic use, the pharmacologically active compounds of this invention will normally be administered as a pharmaceutical composition comprising as the (or an) essential active ingredient at least one such compound in the basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or nonaqueous liquid suspension. The pharmaceutical compositions are prepared by conventional techniques appropriate to the desired preparation.

The dosage to be employed will depend on the age, weight and general health of the patient, as well as the severity of the diarrhea. Generally, however, each dosage unit will contain the active ingredient in an amount of from about 1 to about 100 mg, and preferably from about 5 to about 30 mg. The active ingredient will usually be administered in equal doses from two to four times a day, as necessary.

BIOLOGICAL TESTING

1. Antidiarrheal Activity

A modification of the castor oil test described by Niemegeers [*Arzneim.-Forsch.*, 22, 516–518 (1972)] was used. Male Sprague-Dawley rats (180–220 g) were dosed orally (in one case, subcutaneously) with a test compound or vehicle 1 hour before receiving a standard dose of castor oil orally (3 ml/rat). The rats were individually caged and examined for the presence of diarrhea hourly. Control animals had 100% incidence of diarrhea 1 hour after administering the castor oil. The percentage of rats protected from diarrhea was calculated 1 hour after the castor oil. Six rats were used per dose level.

2. Analgetic Activity

Analgetic activity was determined by the radiant heat method (Rat Tail Flick Test) of D'Amour and Smith [*J. Pharm. Exp. Ther.*, 72, 74–79 (1941)] in Sprague-Dawley male rats (140–180 g). An all or none response was used to determine the dose of test material which produced at least a 100 percent increase in predose response time in 50 percent of the test animals ($ED_{50}$). The $ED_{50}$ values were based on at least 3 doses per drug (6 rats per dose level) and calculated by means of the Finney Dose Response procedure [Finney, D. J., *Probit Analysis*, University Press, Cambridge, England (1971)].

3. Estimation of Physical Dependence Capacity (a) Suppression of withdrawal jumping due to abstinence in withdrawn morphine-dependent mice Mice were treated subcutaneously with gradually increasing doses of morphine sulfate (2, 4, 8, 16 . . . mg/kg) four times daily until 100 mg/kg as a maximal dose was reached. Dosing was continued with 100 mg/kg for the remainder of the four-day test period. An additional subcutaneous injection of 150 mg/kg of morphine base in a sustained release preparation [*Nature*, 237, 220–223 (1972)] was given every evening (4:30 p.m.) to maintain morphine blood levels overnight. A final injection of morphine sulfate at 100 mg/kg was given at 7:30 a.m. on the fifth day.

Six to eight hours after the last dose of morphine, the mice were screened for withdrawal jumping. An animal was considered to be in a state of withdrawal if it exhibited at least five jumps within the observation period of 15 minutes. Only mice that exhibited withdrawal jumping were used. Three test solutions were evaluated in each experiment. One of these solutions was always a control; the other two contained test drugs. All solutions were coded and tested blindly.

Immediately after the mouse was shown to be in a state of withdrawal, the test solution was administered. Fifteen minutes later the mouse was again observed for a period of 15 minutes for withdrawal jumping. If five or more jumps occurred, withdrawal jumping was not considered to have been suppressed by the test drug.

(b) Suppression of body weight loss due to abstinence in withdrawn morphine-dependent rats Male rats, weighing 130–150 g at the beginning of the test, were made dependent to morphine by repeated injections of gradually increasing doses of morphine. The rats were injected subcutaneously with morphine sulfate twice daily (8:00 a.m. and 12:00 noon) with daily increasing doses (20, 40, 80 and 100 mg/kg) for four days. An additional subcutaneous injection of morphine base in a sustained release preparation was given at 4:00 p.m. on the first three days of the study (50, 75 and 100 mg/kg). On the evening of the fourth day morphine sulfate (150 mg/kg) was injected at 4:00 p.m. in place of the suspension of morphine base.

The experimental animals were weighed on the morning of the fifth day at 8:00 a.m. (16 hours after the last dose of morphine) and then were arranged into three groups of six rats per group. The animals were arranged so that the average body weights of the three groups were about the same. Test compounds were then given subcutaneously in place of morphine at 8:00 a.m. and 12:00 noon. The rats were individually weighed at 8:00 a.m. pre-drug and each hour thereafter for eight hours.

The loss in body weight during morphine withdrawal was taken as the index of abstinence. The change in body weight at intervals of 60 minutes was recorded for a period of eight hours. Since one of the test drugs was always saline, the effect of the test drugs on body weight could be compared to that of saline-treated animals.

3. General Procedures

All animals were fasted for 17–20 hours (water ad libitum) before oral administration of test materials. The compounds of Formula I and diphenoxylate were suspended in distilled water containing two drops of Tween 80 and homogenized in a glass homogenizer. Morphine sulfate was dissolved in distilled water. The doses of the compounds of Formula I are in terms of the free base, whereas diphenoxylate and morphine sulfate are expressed in terms of their respective salts.

RESULTS

Table I records the results of experiments designed to determine the degree of dissociation between antidiarrheal and analgetic activity following oral administration to rats. The second and third columns of the table present the results for test compounds as antidiarrheal (castor oil test) and central analgetic agents (rat tail flick), respectively. These findings show that diphenoxylate is the most potent antidiarrheal drug studied followed by Compound d,l-Ib(1) and morphine in order of decreasing potency. It is evident that the relative antidiarrheal specificity (RAS) for morphine is low (14) indicating a poor separation between antidiarrheal and analgetic activity. The RAS for diphenoxylate is 102 showing a tenfold improvement over morphine. However, the RAS value for Compound d,l-Ib(1) is even larger than diphenoxylate, indicating excellent separation between antidiarrheal and analgetic activity following oral administration.

Table II shows the results of a separate test in which the antidiarrheal activity of Compound d,l-Ia(1) was determined after subcutaneous administration and the antidiarrheal activities of d,l-Ib(1), d-Ib(1) and l-Ib(1) were compared after oral administration. It may be seen that the isomorphinan Compound d,l-Ia(1) is a potent antidiarrheal agent and that, with the morphinan Compound Ib(1), the l-isomer is the most potent isomer.

TABLE I

Comparative Antidiarrheal and Central Analgetic Activity

| Compound | $ED_{50}$, mg/kg ORAL (95% Confidence Limits) | | RAS* |
|---|---|---|---|
| | Antidiarrheal Activity Castor Oil Test in Rats | Analgetic Activity Rat Tail Flick | |
| d,l-Ib(1) | 1.41 (0.89–2.25) | >150 | >107 |
| Diphenoxylate | 0.11 (0.05–0.15) | 11.2 (3.0–18.9) | 102 |
| Morphine SO$_4$ | 2.2 (1.5–3.1) | 30.5 (26.3–35.0) | 14 |

*Relative Antidiarrheal Specificity is the Analgetic $ED_{50}$ divided by the Antidiarrheal $ED_{50}$.

TABLE II

| | Antidiarrheal Activity |
|---|---|
| Compound | $ED_{50}$ (95% Confidence Limits) Castor Oil Test in Rats |
| d,l-Ia(1) | 0.56 (0.36–0.88) |
| d,l-Ib(1) | 1.08 (0.76–1.52) |
| l-Ib(1) | 0.64 (0.46–0.86) |
| d-Ib(1) | <1 |

Compound d,l-Ib(1) and diphenoxylate were tested for their ability to supress stereotyped withdrawal jumping in mice, and the results are shown in Table III. No suppressant action was evident for Compound d,l-Ib(1) at doses as high as 27 mg/kg following oral administration. In contrast, diphenoxylate suppressed withdrawal jumping at an oral dose of 9 mg/kg.

TABLE III

Suppression of Withdrawal Jumping in Withdrawn Morphine-Dependent Mice

| Compound | Dose (mg/kg) | Route of Admin. | Percent Suppression |
|---|---|---|---|
| d,l-Ib(1) | 9 | po | 0 |
| d,l-Ib(1) | 27 | po | 0 |
| Diphenoxylate | 9 | po | 56 |
| Morphine SO$_4$ | — | sc | $ED_{50}$ = 1.8 (0.9–3.1) |
| Oxycodone | 10 | po | 100 |

Figure 1:
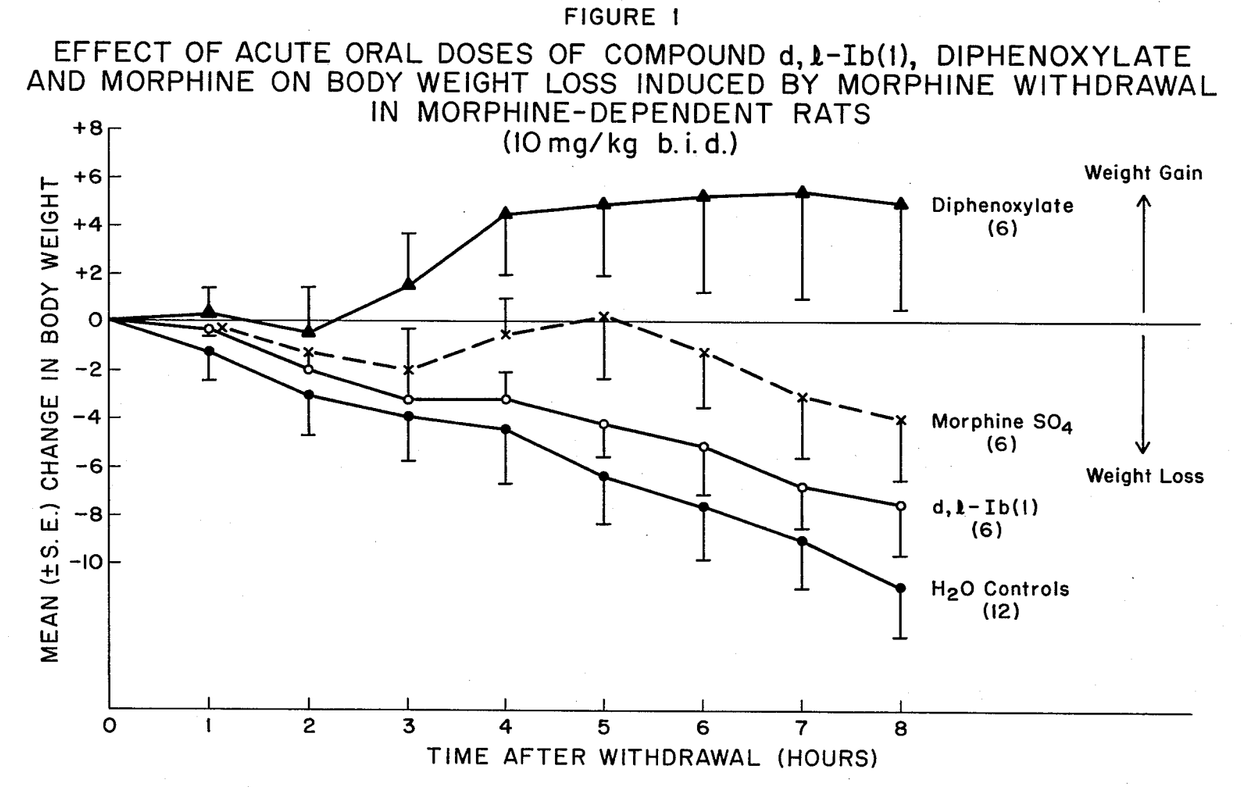
FIG. 1 is a graph comparing a preferred compound of this invention with the known antidiarrheal agents diphenoxylate and morphine, as to their effect on body weight loss induced by morphine withdrawal in morphine-dependent mice.

As a result of the withdrawal of morphine, the body weights of rats chronically treated with morphine decreased markedly and continuously following the injection of saline at the scheduled dosing times (8:00 a.m. and 1:00 p.m.). Physical dependence liability was evaluated in the morphine-dependent rat by measuring the ability of the test drug to prevent the loss of body weight which occurred during withdrawal of morphine. As may be seen from FIG. 1, the ability of diphenoxylate to substitute for morphine was evident following oral administration. By the oral route of administration diphenoxylate was more potent than morphine itself in preventing the loss of body weight due to morphine withdrawal. Contrary to diphenoxylate, no significant prevention of body weight loss occurred following oral administration of Compound d,l-Ib(1).

DESCRIPTION OF THE PREFERRED EMBODIMENTS

EXAMPLE 1 d,l-3-Hydroxy-7-oxo-N-methylmorphinan [Ib(1)]

(A) 3-Methoxy-N-ethoxycarbonyl-7-oxomorphinan (IIIb) and
3-Methoxy-N-ethoxycarbonyl-7-oxoisomorphinan (IIIa)

A mixture of 3-methoxy-N-ethoxycarbonyl-7-oxo-$\Delta^{8,14}$-morphinan (II, 30.0 g), Pd/C (3.0 g, 10%), hydrochloric acid (45 ml conc.) and ethanol (1200 ml) was stirred under a hydrogen atmosphere for 16 hours, and then filtered. The filtrate was neutralized with aqueous sodium bicarbonate and evaporated to a residue. The residue was extracted with chloroform and the combined chloroform extracts were dried over anhydrous sodium sulfate and concentrated to give a crude product (consisting of a 1:1 mixture of IIIb and the corresponding isomorphinan IIIa). The crude product was taken up in benzene and diluted with diethyl ether to crystallize out one isomer (9.6 g). This material melted at 147°–149° C. and, based on NMR spectroscopy, it was assigned the structure 3-methoxy-N-ethoxycarbonyl-7-oxo-isomorphinan IIIa (the 'trans isomer').

Anal. Calc'd for $C_{19}H_{23}NO_4$: C, 69.28; H, 7.04; N, 4.25. Found: C, 69.25; H, 7.15; N, 4.00.

The mother liquor was concentrated to an oil (21 g) consisting mainly of morphinan IIIb which was used for the next step without further purification.

(B) 7,7-Ethylenedioxy-3-methoxy-N-ethoxycarbonylmorphinan (IVb)

A mixture of crude IIIb from Step A (15 g), ethylene glycol (8.5 g), p-toluenesulfonic acid (1 g) and benzene (400 ml) was heated at reflux, and the water produced was separated by a Dean-Stark water separator. After the expected amount of water was collected, the mixture was concentrated to a volume of 150 ml, cooled and washed with water to remove excess ethylene glycol. The resulting benzene solution was dried over anhydrous sodium sulfate and concentrated to an oil (17 g) which give IR and NMR spectra that were consistant with the expected structure. This material was used for the next step without further purification.

(C) 7,7-Ethylenedioxy-3-methoxy-N-methylmorphinan (Vb)

To a suspension of LiAlH$_4$ (2.0 g, 50.13 mmoles) in anhydrous diethyl ether (100 ml) was added dropwise a solution of crude IVb (17.0 g), in 100 ml of anhydrous diethyl ether and, after the addition was completed, the mixture was heated at reflux for 2 hours. After cooling, the reaction mixture was treated with water (12 ml) and sodium hydroxide (3 ml of 5 N). The reaction mixture was filtered and the filtrate was concentrated to give a residue (13.6 g). Based on NMR spectroscopy, the residue consisted mainly of the expected Vb. This material was purified by column chromatography. (Alumina activity 1, 780 g, eluted first with benzene:diethyl ether (60:40) then with diethyl ether). Two major fractions were obtained: A (5.2 g) and B (5.7 g). Fraction B was quite pure but fraction A still contained some of the corresponding 'trans isomer' (isomorphinan) and was rechromatographed to give 4.2 g of pure Vb as oil (total yield 9.9 g) plus the corresponding isomorphinan Va.

(D) 3-Methoxy-7-oxo-N-methylmorphinan (VIb)

Compound Vb from Step C (1.4 g of oil) was treated with sulfuric acid (30 ml of 3 N) at 80° C. for 1 hour. The reaction mixture was made basic with ammonium hydroxide and extracted with chloroform. The combined chloroform extracts were dried over anhydrous sodium sulfate and concentrated to give a residue (1.24 g) which was recrystallized from diethyl ether to give colorless prisms mp 110°–111° C. The structure was confirmed by IR and NMR spectroscopies.

Anal. Calc'd for $C_{18}H_{23}NO_2$: C, 75.75; H, 8.12; N, 4.91. Found: C, 75.86; H, 8.16; N, 4.83.

The corresponding 'trans isomer' (isomorphinan) VIa was prepared from Va in a similar manner and had a mp of 139°–140° C.

(E) d,l-3-Hydroxy-7-oxo-N-methylmorphinan [Ib(1)]

Compound Vb from Step C (1 g) was treated with hydrobromic acid (48%, 11 ml) at reflux temperature for 45 minutes. The mixture, after cooling, was made basic with ammonium hydroxide and extracted with chloroform. The combined chloroform extracts were dried over anhydrous sodium sulfate and concentrated to give crude product (0.73 g). The crude material was taken up in methanol and diluted with benzene to crystallize out the product. This material had mp 212°–214° C. (decomp.) and its structure was confirmed by IR and NMR spectroscopies.

Anal. Calc'd for $C_{17}H_{21}NO_2$: C, 75.24; H, 7.80; N, 5.16. Found: C, 75.16; H, 7.97; N, 4.99.

Compound Ib(1) was also prepared by treatment of Compound VIb (from Step D) with hydrobromic acid as described above, and was found to be identical with the Compound Ib(1) prepared directly from Compound Vb.

EXAMPLE 2 d,l-3-Hydroxy-7-oxo-N-methylmorphinan [Ib(1)]

(A) 7,7-Ethylenedioxy-14-hydroxy-3-methoxy-N-methylisomorphinan (VIIIa)

A mixture of 7,7-ethylenedioxy-14-hydroxy-3-methoxyisomorphinan (VIIa, 6.6 g), formaldehyde (6.6 g of 37%) and formic acid (2.4 g) was stirred at room temperature until gas evolution ceased, and was then heated at reflux temperature for 3 hours. After cooling, the reaction mixture was poured into ice water and made basic with 3 N sodium hydroxide solution. The crude solid product was collected by filtration and air dried. The crude product was recrystallized from diethyl ether to give 6 g of Compound VIIIa. The structure was confirmed by NMR spectroscopy. mp 130° C.

Anal. Calc'd for $C_{20}H_{27}NO_4$: C, 69.54; H, 7.88; N, 4.06. Found: C, 70.10; H, 7.97; N, 3.73.

(B) 3-Methoxy-N-methyl-7-oxo-$\Delta^{8,14}$-morphinan (IX)

Compound VIIIa (0.5 g) from Step A was dissolved in 10 ml of acetone and made acidic with gaseous hydrogen chloride. The resulting salt was warmed on a steam bath for 1 hour and then allowed to stand at room temperature overnight. The acetone was evaporated and the residue was taken up in 10 ml of water and made basic with concentrated ammonia. The product was extracted into diethyl ether (2×15 ml) and dried over anhydrous potassium carbonate. The ether was evaporated and the residue redissolved in isopropyl alcohol (10 ml), and hydrogen chloride was added to form a salt which crystallized out. The salt was converted to the free base and recrystallized from diethyl ether to give a product with mp 84°–85° C. Its IR and NMR spectra were consistent with the expected structure.

Anal. Calc'd for $C_{18}H_{21}NO_2$: C, 76.29; H, 7.47; N, 4.94. Found: C, 76.17; H, 7.53; N, 4.66.

Alternatively, Steps A and B, above, may be combined as follows.

(AB) 3-Methoxy-N-methyl-7-oxo-$\Delta^{8,14}$-morphinan hydrochloride (IX)

A mixture of formic acid (21.3 g) and formaldehyde (13 ml, 37%) was added portionwise to 7,7-ethylenedioxy-14-hydroxy-3-methylisomorphinan (VIIa, 20 g). After foaming ceased, the mixture was heated gently at reflux for 4 hours. The reaction mixture was cooled and poured into a mixture of ice and aqueous sodium hydroxide (100 ml of 10%). The crude product mixture was extracted into chloroform, washed with water and dried over anhydrous magnesium sulfate. The chloroform was evaporated and replaced with acetone (150 ml), and hydrogen chloride (as an acetone solution) was then added. The precipitated salt was filtered off and washed with acetone (yield 11.0 g). This material was used in Step D(1) without further purification.

(C) 3-Hydroxy-N-methyl-7-oxo-$\Delta^{8,14}$-morphinan Hydrochloride (X)

A solution of 3-methoxy-N-methyl-7oxo-$\Delta^{8,14}$-morphinan from Step B (5 g) in 50 ml of 48% aqueous hydrobromic acid was heated at reflux for 45 minutes. The reaction mixture was cooled and poured into a mixture of ice (100 g) and concentrated ammonia (50 ml), and stirred for 0.5 hour. The mixture was extracted with chloroform (3×30 ml) and dried over anhydrous magnesium sulfate. After evaporating the solvent, the residue was dissolved in acetone (50 ml) and a small amount of insoluble material was filtered off. To the filtrate was added hydrochloric acid (0.46 g in acetone) and the resulting crystalline salt was collected and dried (yield 2.75 g). This material was used in Step D(2) without further purification.

(D) d,l-3-Hydroxy-7-oxo-N-methylmorphinan [Ib(1)]

(1) Crude 3-methoxy-N-methyl-7-oxo-$\Delta^{8,14}$-morphinan hydrochloride (from Step AB) (2.5 g) was dissolved in 200 ml 95% ethanol in a hydrogenation bottle to which Pd/C (0.5 g, Englehard) was added and the mixture was shaken under 30 psi of hydrogen at room temperature for 2 hours. Filtration and evaporation gives a gummy residue which was dissolved in water. The solution was made alkaline with ammonia and extracted with chloroform. The combined extracts were dried over magnesium sulfate and concentrated to give an oil (2.2 g) [TLC indicated the product to consist of morphinan VIb (cis) and isomorphinan VIa (trans) in the ratio of about 5:1]. The isomers were separated by chromatography on silica gel column utilizing chloroform: methanol (90:10) as eluant. The VIb isolated was identical to that obtained in Example 1, Step D. Treatment of VIb with 48% hydrobromic acid as in Example 1, Step E, gives Ib(1) which is shown by IR and NMR to be identical to that obtained in Example 1, Step E.

(2) The hydrochloride salt of X from Step C (2.75 g, 9 mmole) was dissolved in 50 ml ethanol in a hydrogenation bottle, to which was added 10% Pd/C (0.5 g, Englehard) and the mixture was shaken under 30 psi of hydrogen for 2 hours. The reaction mixture was filtered and the filtrate evaporated to give an oil which was redissolved in water. The solution was made alkaline with ammonia and extracted with chloroform. The combined extract was dried over anhydrous magnesium sulfate and concentrated to an oil (1.3 g) which solidified upon trituration with diethyl ether [TLC indicated the ratio of morphinan Ib(1) (cis) to isomorphinan Ia(1) (trans) to be about 5:1]. The isomers are separated by chromatography on silica gel column utilizing chloroform:methanol (90:10) as eluant to give pure compound Ib(1) which is shown by IR and NMR to be identical with that obtained in Example 1, Step E, and Compound Ia(1).

EXAMPLE 3 d,l-3-Hydroxy-7-oxo-N-methylisomorphinan [Ia(1)]

7,7-Ethylenedioxy-3-methoxy-N-methylisomorphinan Va obtained from Example 1, Step C was treated with hydrobromic acid according to the general procedure described in Example 1, Step E, to produce d,l-3-hydroxy-7-oxo-N-methylisomorphinan Ia(1). Its hydrochloride salt melted at 260°–265° C. (decomp.).

EXAMPLE 4 d,l-3-Hydroxy-7-oxo-N-methylisomorphinan [Ia(1)]

(A)
7,7-Ethylenedioxy-3-methoxy-N-ethoxycarbonylisomorphinan (IVa)

A mixture of IIIa obtained in Example 1, Step A, (8.6 g), ethylene glycol (4.5 ml) and p-toluenesulfonic acid (0.55 g) in 250 ml of benzene was heated at reflux for 6 hours using a Dean-Stark apparatus to remove the water formed. After cooling, the mixture was washed with water, dried over anhydrous sodium sulfate and then concentrated to give 7.8 g of IVa. A sample was recrystallized from diethyl ether, mp 114°–115° C.

Anal. Calc'd for $C_{21}H_{27}NO_5$: C, 67.54; H, 7.29; N, 3.75. Found: C, 67.47; H, 7.38; N, 3.62.

(B) 3-Methoxy-N-methylisomorphinan (VIa)

Compound IVa (1.5 g) from Step A in THF (15 ml) was slowly added to 1 g of lithium aluminum hydride (LAH) that was suspended in 15 ml of THF. The resulting mixture was heated at reflux for 1.5 hours, cooled and excess LAH destroyed with Rochelle salt solution. The mixture was extracted with chloroform (3×20 ml) and the chloroform solution was concentrated to give crude Va as a gum. This was dissolved in 20 ml of 3 N $H_2SO_4$, allowed to stand overnight at room temperature, made alkaline with ammonia and then extracted with chloroform. The combined extract was dried over anhydrous magnesium sulfate and concentrated to give a residue which crystallized from diethyl ether to give VIa (0.78 g) mp 138°–139° C. Its IR and NMR spectra were consistent with the expected structure.

Anal. Calc'd for $C_{18}H_{23}NO_3$: C, 75.75; H, 8.12; N, 4.91. Found: C, 75,56; H, 8.16; N, 4.83.

(C) 3-Hydroxy-7-oxo-N-methylisomorphinan [Ia(1)]

Compound VIa from Step B was dissolved in 60 ml of methylene chloride and cooled to 0° C. Boron tribromide (7.5 ml in 20 ml of methylene chloride) was added dropwise over a period of 10 minutes. The mixture was allowed to stand at 0° C. for 1 hour and water (30 ml) was then added. The methylene chloride layer was separated and the aqueous layer was heated at 70°–75° C. for 1 hour. After cooling, the aqueous solution was made alkaline with ammonia and extracted with methylene chloride (3×75 ml). After drying over anhydrous magnesium sulfate, the methylene chloride extract was evaporated to give a residue which was purified by chromatography (alumina, eluted with a mixture consisting of diethyl ether 50%, benzene 46% and methanol 4%). The free base isolated from the column was made into hydrochloride salt in methanol (yield 245 mg) mp 255°–265° C. Its IR and NMR spectra were consistent with the expected structure.

Anal. Calc'd for $C_{17}H_{21}NO_2 \cdot \frac{1}{2}H_2O \cdot HCl$: C, 64.45; H, 7.32; N, 4.42. Found: C, 63.97; H, 7.30; N, 4.19.

EXAMPLE 5

Optical Resolution of d,l-7,7-Ethylenedioxy-14-hydroxy-3-methoxyisomorphinan (d,l-VIIa)

(A)

l-7,7-Ethylenedioxy-14-hydroxy-3-methoxyisomorphinan (l-VIa)

d,l-7,7-Ethylenedioxy-14-hydroxy-3-methoxyisomorphinan (0.99 g, 299 mmole) was dissolved in chloroform (10 ml), to which was added a solution of dibenzoyl-d-tartaric acid monohydrate (1.12 g, 1 equiv.) in acetone (10 ml). The resulting solution was evaporated to give a foam that was dissolved in acetone (30 ml) and allowed to stand for 2 days. The precipitated crystals were then filtered off. Yield 0.84 g (40%), $[\alpha]_D$ −86.9° (c, 0.3, CH$_3$OH). The salt was recrystallized from methanol/water; yield 79%, $[\alpha]_D$ −99.4° (c, 0.3, CH$_3$OH); the l-isomorphinan free base had an $[\alpha]_D$ −76.6° (c, 0.3, CHCl$_3$).

(B)

d-7,7-Ethylenedioxy-14-hydroxy-3-methoxyisomorphinan (d-VIa)

The mother liquor from Step A was evaporated and the d-rich free base was generated (0.5 g, 1.51 mmole). This was dissolved in chloroform (10 ml), to which was added a solution of dibenzoyl-l-tartaric acid monohydrate (0.568 g, 1 equiv.) in acetone (5 ml). The resulting solution was evaporated to give a foam that was dissolved in acetone (6 ml), from which crystallization gradually took place with stirring. The salt was filtered off after 2 hours; yield of the l-salt of the d-isomorphinan was 0.51 g (48%), $[\alpha]_D$ +94.2° (c, 0.3, CH$_3$OH).

EXAMPLE 6

Optical Resolution of d,l-7,7-Ethylenedioxy-14-hydroxy-3-methoxyisomorphinan (d,l-VIIa)

(A)

d-7,7-Ethylenedioxy-14-hydroxy-3-methoxyisomorphinan (d-VIIa)

d,l-7,7-Ethylendioxy-14-hydroxy-3-methoxyisomorphinan (11.3 g, 0.0341 mole) was dissolved in chloroform (100 ml) and treated with a solution of dibenzoyl-l-tartaric acid monohydrate (12.8 g, 1 equiv.) in acetone (60 ml). The resulting solution was evaporated to give a white foam which was dissolved in methanol (100 ml), from which precipitation took place shortly after dissolution. In order to re-dissolve the salt, more methanol (550 ml) was added with heating and then 400 ml water was added. The whole solution was concentrated on a rotary evaporator until precipitation began and was then stirred overnight. The precipitated crystals were filtered off. Yield of the l-salt of the d-isomorphinan was 10.2 g (42.3%), $[\alpha]_D$ +85.1° (c, 0.3, CH$_3$OH); the free base had $[\alpha]_D$ +76.4° (c, 0.3, CHCl$_3$).

(B)

l-7,7-Ethylenedioxy-14-hydroxy-3-methoxyisomorphinan (l-VIIa)

The mother liquor from Step A was evaporated and the l-rich free base was generated (3.53 g, 10.66 mmole). This was dissolved in chloroform (30 ml), to which was added a solution of dibenzoyl-d-tartaric acid monohydrate (4.01 g, 10.66 mmole) in acetone (20 ml). The resulting solution was evaporated to give a foam that was dissolved in acetone (50 ml), from which crystallization gradually took place with stirring. The salt was filtered off after 3 hours; yield of the d-salt of the l-isomorphinan was 4.93 g (20%), $[\alpha]_D$ −98.2° (c, 0.3, CH$_3$OH).

EXAMPLE 7 l-3-Hydroxy-N-methyl-7-oxomorphinan [l-Ib(1)]

(A) l-3-Methoxy-N-methyl-7-oxo-$\Delta^{8,14}$-morphinan hydrochloride (l-IX)

A mixture of l-7,7-ethylenedioxy-14-hydroxy-3-methoxyisomorphinan (l-VIIIa) (3.57 g, 0.0108 mole, $[\alpha]_D$ −76.6° (CHCl$_3$)), formaldehyde (5 ml, 37%) and formic acid (8.3 g) was stirred at room temperature until gas evolution ceased, and then was heated at reflux temperature for 3 hours. After cooling, the reaction mixture was poured into ice water, made alkaline with 10% sodium hydroxide solution and extracted with chloroform. The chloroform extract was dried over anhydrous magnesium sulfate and evaporated to give an oil (~3 g, $[\alpha]_D$ −36.4° (CHCl$_3$)) that was converted to its hydrochloride in acetone. Yield 2.78 g (80.6%), mp 230°–232° (dec.). The structure was confirmed by IR and NMR: IR (CHCl$_3$) $\nu_{max}$ 1660 cm$^{-1}$ (C0); NMR (CDCl$_3$) δ2.48 (s, 3H, NCH$_3$), 3.83 (s, 3H, CH$_3$O), 5.98 (s, 1H, vinyl H).

(B) l-3-Methoxy-N-methyl-7-oxomorphinan (l-VIb)

A solution of l-3-methoxy-N-methyl-7-oxo-$\Delta^{8,14}$-morphinan hydrochloride (l-IX) (2.6 g, 8.0 mmole) in 95% ethanol (120 ml) was shaken with 10% Pd/C (0.5 g) under 30 psi of hydrogen for 2 hours. The reaction mixture was filtered through diatomaceous earth and the filtrate was evaporated to give an oil which was dissolved in water, made alkaline with conc. ammonium hydroxide and extracted with chloroform. The chloroform extract was dried over anhydrous magnesium sulfate and evaporated to give an oil (2.0 g). The product was isolated by column chromatography (silica gel, chloroform/10% methanol); yield 1.55 g (68%) of an oil $[\alpha]_D$ −56.3° (c, 0.3, CHCl$_3$). The structure was confirmed by IR and NMR spectroscopies: IR (neat) $\nu_{max}$ 1700 cm$^{-1}$ (C0); NMR (CDCl$_3$) δ2.42 (s, 3H, NCH$_3$) 3.82 (s, 3H, CH$_3$O).

(C) l-3-Hydroxy-N-methyl-7-oxomorphinan [l-Ib(1)]

l-3-Methoxy-N-methyl-7-oxomorphinan (l-VIb) (1.2 g, 4.2 mmole) was treated with HBr (12 ml, 48%) at reflux temperature for 0.5 hour. The reaction mixture was cooled, poured into ice water, made alkaline with conc. ammonium hydroxide and extracted with chloroform. The chloroform extract was dried over anhydrous magnesium sulfate and evaporated to give a foam (1.14 g). The pure product was obtained by column chromatography (silica gel, chloroform/10% methanol saturated with conc. ammonium hydroxide). Yield 0.36 g (32%), colorless crystals, mp 116°–120°, $[\alpha]_D$ −56.1° (c, 0.3, CHCl$_3$). The structure was confirmed by IR and NMR spectroscopies: IR (nujol) $\nu_{max}$ 1715 cm$^{-1}$ (CO), NMR (CDCl$_3$) δ2.47 (NCH$_3$).

EXAMPLE 8 d-3-Hydroxy-N-methyl-7-oxomorphinan [d-Ib(1)]

(A) d-3-Hydroxy-N-methyl-7-oxo-Δ$^{8,14}$-morphinan (d-X)

To d-7,7-ethylenedioxy-14-hydroxy-3-methoxyisomorphinan (d-VIIa) from Example 6, Step A (3.92 g, 0.012 mole) was added a mixture of 8.3 g of formic acid and 5 ml of 37% formaldehyde. The resulting solution was refluxed for 3 hours, cooled and poured into a mixture of 35 ml (10%) sodium hydroxide and ice. The mixture was extracted with chloroform and the combined extract was dried over anhydrous magnesium sulfate and then concentrated to give an oil (3.92 g) which was redissolved in 20 ml of acetone. Hydrogen chloride gas was bubbled into this solution to obtain the salt, which was collected on a filter and washed with acetone. The free base was regenerated and had a rotation $[\alpha]_D$ +34.9° (0.3, CHCl$_3$), and its IR and NMR spectra were consistent with the expected structure (d-IX). Compound d-IX hydrochloride (2.0 g, 6 mmole) was treated with HBr (48%, 20 ml) at reflux temperature for 1 hour. The reaction mixture was poured into a mixture of ammonium hydroxide and ice, and extracted with chloroform. The extract was dried over anhydrous magnesium sulfate and evaporated to give an oil. The product was isolated by column chromatography (silica gel, chloroform/10% methanol). Yield 0.8 g (50%), $[\alpha]_D$ +48.8° (c, 0.3, CHCl$_3$). The structure was confirmed by IR and NMR spectroscopies: NMR (CDCl$_3$) δ2.48 (NCH$_3$), 5.95 (vinyl H).

(B) d-3-Hydroxy-N-methyl-7-oxomorphinan [d-Ib(1)]

A solution of d-3-hydroxy-N-methyl-7-oxo-Δ$^{8,14}$-morphinan hydrochloride (d-X) (0.66 g, 2.16 mmole) in 50 ml of ethanol was placed in a hydrogenation bottle with 10% Pd/C (0.22 g) and shaken at room temperature under 30 psi of hydrogen for 2 hours. The reaction mixture was filtered through diatomaceous earth and the filtrate was evaporated to give an oil which was dissolved in water, made alkaline with ammonium hydroxide and extracted with chloroform. The chloroform extract was dried over anhydrous magnesium sulfate and evaporated to give a white foam which was purified by column chromatography (silica gel, CHCl$_3$/10% CH$_3$OH). Yield 0.41 g (70%), white crystals, $[\alpha]_D$ +58.9° (c, 0.3, CHCl$_3$). The structure was confirmed by IR and NMR spectroscopies.

Example 9 d,l-3-Hydroxy-7-oxo-N-cyclopropylmethylmorphinan [Ib(2); R$^2$=cyclopropyl]

(A) 7,7-Ethylenedioxy-3-methoxymorphinan (XIXb)

The crude IVb from Step B in Example 1 (containing a small amount of IVa) (10 g) in 150 ml of ethylene glycol and 100 ml in 45% aqueous KOH was heated at reflux temperature under nitrogen for 24 hours. After cooling, the mixture was poured into water (500 ml) and extracted with chloroform (2×100 ml). The chloroform solution was acidified with sulfuric acid (3 N), and the acidic aqueous phase was separated, made alkaline with sodium hydroxide (3 N) and extracted with methylene chloride (3×50 ml). The combined methylene chloride extract was dried over anhydrous magnesium sulfate and concentrated to give a residue (5.0 g). Its IR and NMR spectra were consistent with the structure but some ketal (7,7-ethylenedioxy moiety) had been hydrolyzed during "work up" to give some ketone (7-oxo moiety). This mixture was used for Step B.

(B)

7,7-Ethylenedioxy-3-methoxy-N-cyclopropylmethylmorphinan (XIVb; R$^2$=cyclopropyl)

The mixture of 7,7-ethylenedioxy-3-methoxymorphinan and 3-methoxy-7-oxomorphinan (containing a small amount of the two corresponding isomorphinans) from Step A (5 g) in 150 ml of dry CH$_2$Cl$_2$ containing 7.0 ml of pyridine was cooled to 0° C., and a solution of cyclopropane carboxylic acid chloride (3.45 g) in 40 ml of dry methylene chloride was added dropwise, but rapidly. The reaction mixture was allowed to stir an additional 20 minutes at 0° C. It was then washed with water, dried and evaporated to dryness. Benzene was added and evaporated several times to remove the pyridine. The product, which was a mixture of 3-methoxy-7,7-ethylenedioxy-N-cyclopropylcarbonylmorphinan (XIIIb; R$^2$=cyclopropyl) and the corresponding 7-oxo compound was then converted completely to the 7,7-ethylenedioxy compound by refluxing it overnight in benzene containing 0.35 g of p-toluenesulfonic acid and 2.7 ml of ethylene glycol. The benzene solution was then washed with water, dried and evaporated to dryness. The solid was dissolved in dry ether, 3.3 g of lithium aluminum hydride was added, and the mixture was refluxed for one hour. After cooling, a saturated aqueous solution of Rochelle salt was added and the aqueous phase was extracted with three portions of chloroform. The combined chloroform layers were dried and evaporated to dryness. The product was chromatographed on an alumina column using chloroform as eluant. There was obtained 3.7 g of the title morphinan plus 0.77 g of the corresponding isomorphinan.

A portion of the morphinan was dissolved in ether and a solution of oxalic acid in ether was added. The precipitated salt was removed by filtration and twice recrystallized from isopropanol; mp 174°–176° C.

Anal. Calc'd for C$_{23}$H$_{31}$NO$_3$.1½C$_2$H$_2$O$_4$: C, 61.89; H, 6.79; N, 2.77. Found: C, 61.73; H, 6.86; N, 2.62.

After an additional recrystallization from isopropanol, the oxalate salt melted at 176°–178° C. (decomp.).

(C)

7,7-Ethylenedioxy-3-hydroxy-N-cyclopropylmethylmorphinan (XVb; R$^2$=cyclopropyl)

Sodium hydride (2.49 g of 57% in oil, washed twice with benzene) in 80 ml of dry dimethylformamide was cooled to 0° C. in a nitrogen atmosphere, and 4.77 ml of ethyl mercaptan was slowly added. To this pre-formed solution of sodium thioethoxide was slowly added a solution of 7,7-ethylenedioxy-3-methoxy-N-cyclopropylmethylmorphinan (2.2 g) in 20 ml of dimethylformamide. The mixture was refluxed for three hours, cooled, poured into an ice-water mixture, adjusted to pH 8 and extracted with four portions of methylene chloride. The combined extracts were evaporated to dryness, first on a hot water bath and then under high vacuum. The crude product was chromatographed on an alumina column using methanol:ether:benzene (2:30:68) as eluant. The eluate was evaporated to dryness to give 1.73 g (81%) of 7,7-ethylenedioxy-3-hydroxy-N-cyclopropylmethylmorphinan. The product still had some odor of dimethylformamide, so one-half of it was re-chromatographed and then twice recrystallized from ether to give 0.53 g of pure material.

Anal. Calc'd for $C_{22}H_{29}NO_3$: C, 74.33; H, 8.22; N, 3.94. Found: C, 73.90; H, 8.22; N, 3.78.

(D)
d,l-3-Hydroxy-7-oxo-N-cyclopropylmethylmorphinan [Ib(2); $R^2$=cyclopropyl]

7,7-Ethylenedioxy-3-hydroxy-N-cyclopropylmethylmorphinan (0.6 g) was dissolved in ether containing a small amount of methylene chloride. HCl gas was bubbled into the solution, and the resulting precipitate was removed by filtration and dissolved in a mixture of methylene chloride and methanol. Ammonia gas was bubbled into the solution and the precipitate was removed by filtration. The filtrate was evaporated to dryness and the solid was twice recrystallized from ether. Yield 150 mg (29%).

Anal. Calc'd for $C_{20}H_{27}NO.\frac{1}{4}H_2O$: C, 76.03; H, 8.13; N, 4.33. Found: C, 76.12; H, 7.97; N, 4.29.

EXAMPLE 10 d,l-3-Hydroxy-7-oxo-N-cyclopropylmethylisomorphinan [Ia(2); $R^2$=cyclopropyl]

(A) 7,7-Ethylenedioxy-3-methoxyisomorphinan (XIXa)

A mixture of 7,7-ethylenedioxy-3-methoxy-N-ethoxycarbonylisomorphinan from Example 4, Step A, (1 g), ethylene glycol (15 ml) and aqueous KOH (10 ml of 45%) was refluxed under a nitrogen atmosphere for 24 hours. The mixture was then cooled, water was added, and the aqueous mixture was extracted with three portions of methylene chloride. The combined methylene chloride layers were extracted with 3 N $H_2SO_4$ (ice cold; rapidly), and the aqueous acidic phase was made basic with 3 N NaOH and was extracted with methylene chloride. The extract was dried and evaporated to dryness to give 0.47 g of the title product (56%). The structure of the product was confirmed by IR and NMR spectroscopies. It has mp 165°-168° C.

Anal. Calc'd for $C_{19}H_{25}NO_3$: C, 72.35; H, 7.99; N, 4.44. Found: C, 72.40; H, 8.05; N, 4.42.

(B)
7,7-Ethylenedioxy-3-methoxy-N-cyclopropylcarbonylisomorphinan (XIIIa; $R^2$=cyclopropyl)

To an ice-cold solution of 7,7-ethylenedioxy-3-methoxyisomorphinan (1.45 g) in methylene chloride (10 ml) containing pyridine (2 ml) was slowly added an ice-cold solution of cyclopropane carboxylic acid chloride (1.0 g) in methylene chloride. After the addition was complete, the reaction mixture was allowed to stir an additional 20 minutes at 0° C. The reaction mixture was then washed with water, dried and evaporated to dryness. Benzene was added and evaporated several times to remove the pyridine. A nearly quantitative yield of the title product was obtained. The structure of the product was confirmed by IR and NMR spectroscopies. It has mp 143°-145° C.

Anal. Calc'd for $C_{23}H_{29}NO_4$: C, 72.04; H, 7.62, N, 3.65. Found: C, 71.81; H, 7.56; N, 3.60.

(C)
7,7-Ethylenedioxy-3-methoxy-N-cyclopropylmethylisomorphinan (XIVa; $R^2$=cyclopropyl)

To a solution of 7,7-ethylenedioxy-3-methoxy-N-cyclopropylcarbonylisomorphinan (1.4 g) in dry tetrahydrofuran (50 ml) was carefully added 0.7 g of lithium aluminum hydride, and the mixture was refluxed for one hour. After cooling, a saturated aqueous solution of Rochelle salt was added, and the aqueous phase was extracted with three portions of chloroform. The combined chloroform layers were dried and evaporated to dryness to give 1.32 g of product. Thin layer chromatography showed just a trace of impurity. NMR showed that the product contained about 16% benzene. Actual yield was 1.1 g (84%).

(D)
d,l-3-Hydroxy-7-oxo-N-cyclopropylmethylisomorphinan

Sodium hydride (0.88 g of 57% in oil, washed twice with benzene) in 40 ml of dry dimethylformamide was cooled to 0° C. in a nitrogen atmosphere, and 1.7 ml of ethyl mercaptan was slowly added. To this pre-formed solution of sodium thioethoxide was slowly added a solution of 7,7-ethylenedioxy-3-methoxy-N-cyclopropylmethylisomorphinan (0.77 g) in 10 ml of dimethylformamide. The mixture was refluxed for three hours, cooled, poured into an ice-water mixture, adjusted to pH 8 and extracted with four portions of methylene chloride. The combined extracts were evaporated to dryness, first on a hot water bath and then under high vacuum. The crude product was chromatographed on an alumina column using methanol:ether:benzene (2:30:68) as eluant. The eluate was evaporated to dryness to give 0.56 g of 7,7-ethylenedioxy-3-hydroxy-N-cyclopropylmethylisomorphinan (XVa; $R^2$=cyclopropyl), which was hydrolyzed with 12 M HCl and the made basic with concentrated aqueous $NH_4OH$ to liberate the free base of the tile product. The product was extracted into methylene chloride and the methylene chloride solution was dried over anhydrous sodium sulfate. The solution was concentrated and the residue was purified by column chromatography (alumina, eluted with chloroform:methanol 98:4). The eluant was evaporated and the residue recrystallized from diethyl ether. Its structure was confirmed by IR and NMR spectroscopies and it had an mp 180°-182° C.

Anal. Calc'd for $C_{20}H_{25}NO_2$: C, 77.14; H, 8.09; N, 4.50. Found: C, 76.98; H, 8.22; N, 4.33.

To 470 mg of the free base dissolved in ether was added a solution of oxalic acid in ether, until precipitation stopped. The solid was recovered by filtration and twice recrystallized from isopropanol. Yield of the oxalate salt was 360 mg; mp 208°-210° C.

Anal. Calc'd for $C_{22}H_{29}NO_3.2C_2H_2O_4$: C, 64.70; H, 7.01; N, 3.14. Found: C, 64.86; H, 7.01; N, 3.14.

EXAMPLE 11 d,l-3-Hydroxy-7-oxo-N-cyclobutylmethylmorphinan

The general procedure of Example 9 is repeated except that the cyclopropane carboxylic acid chloride utilized therein is replaced by an equimolar amount of cyclobutane carboxylic acid chloride, and d,l-3- hydroxy-7-oxo-N-cyclobutylmethylmorphinan is thereby produced.

Example 12 d,l-3-Hydroxy-7-oxo-N-cyclobutylmethylisomorphinan

The general procedure of Example 10 is repeated except that the cyclopropane carboxylic acid chloride utilized therein is replaced by an equimolar amount of cyclobutane carboxylic acid chloride, and d,l-3-hydroxy-7-oxo-N-cyclobutylmethylisomorphinan is thereby produced.

Example 13 d,l-3-Hydroxy-7-oxomorphinan (XVIIIb)

(A) d,l-3-Methoxy-7-oxo-$\Delta^{8,14}$-isomorphinan Hydrochloride (XXa)

d,l-7-Ethylenedioxy-14-hydroxy-3-methoxyisomorphinan (VIIa) (3.3 g) in 30 ml of acetone was treated with HCl gas until acidic and then stirred at room temperature overnight. The solid which formed was collected on a filter and recrystallized from methanol to yield 2.5 g (92%). It had mp 195° C. (decomp.) and its IR and NMR spectra were consistent with the expected structure.

Anal. Calc'd for $C_{17}H_{19}NO_2 \cdot HCl \cdot H_2O$: C, 63.05; H, 6.84; N, 4.32. Found: C, 63.11; H, 6.61; N, 4.30.

(B) d,l-3-Hydroxy-7-oxomorphinan (XVIIIb)

The hydrochloride salt from Step A is hydrogenated by the general procedure of Example 2, Step D(1), and, after chromatography on silica gel, gives primarily the title product, with only a trace of the corresponding isomorphinan. Its IR and NMR spectra are consistent with the expected structure.

Example 14 d,l-3-Hydroxy-7-oxoisomorphinan (XVIIIa)

Sodium hydride (0.88 g of 57% in oil, washed twice with benzene) in 40 ml of dry dimethylformamide (DMF) is cooled to 0° C. under nitrogen atmosphere and 1.7 ml of ethylmercaptan is slowly added. To this preformed solution of sodium thioethoxide is slowly added a solution of 7,7-ethylenedioxy-3-methoxyisomorphinan from Example 10, Step A, (0.7 g) in 10 ml of DMF. The mixture is refluxed for 3 hours, cooled and poured into ice water. The mixture is extracted with methylene chloride (4×15 ml) and the combined extract is concentrated to a residue which is dissolved in aqueous hydrochloric acid (12N), made alkaline with concentrated ammonia and extracted with chloroform. The chloroform extract is dried over anhydrous sodium sulfate and concentrated to give the title product as a foam. Its IR and NMR spectra are consistent with the structure.

Example 15 d,l-3-Hydroxy-7-oxo-N-propargylmorphinan Hydrochloride

To a stirred mixture of d,l-3-hydroxy-7-oxomorphinan (XVIIIb) and about 5 molar equivalents of triethylamine in absolute ethanol, under a nitrogen atmosphere, at room temperature, is added about 1.5 molar equivalents of propargyl bromide in absolute ethanol. After the addition is complete, the reaction mixture is refluxed for about eighteen hours and then evaporated to dryness. The residue is mixed with 20% aqueous $Na_2CO_3$ solution and the mixture is extracted with several portions of ether. The combined ether extracts are dried over $Na_2SO_4$ and filtered. The resulting solution is filtered through a diatomaceous earth-charcoal mixture and concentrated at reduced pressure to an oil. The oil is taken up in ether and HCl gas is bubbled into the solution to give d,l-3-hydroxy-7-oxo-N-propargylmorphinan hydrochloride.

Example 16 d,l-3-Hydroxy-7-oxo-N-propargylisomorphinan Hydrochloride

To a stirred mixture of d,l-3-hydroxy-7-oxoisomorphinan (XVIIIa) and about 5 molar equivalents of triethylamine in absolute ethanol, under a nitrogen atmosphere, at room temperature, is added about 1.5 molar equivalents of propargyl bromide in absolute ethanol. After the addition is complete, the reaction mixture is refluxed for about eighteen hours and then evaporated to dryness. The residue is mixed with 20% aqueous $Na_2CO_3$ solution and the mixture is extracted with several portions of ether. The combined ether extracts are dried over $Na_2SO_4$ and filtered. The resulting solution is filtered through a diatomaceous earth-charcoal mixture and concentrated at reduced pressure to an oil. The oil is taken up in ether and HCl gas is bubbled into the solution to give d,l-3-hydroxy-7-oxo-N-propargylisomorphinan hydrochloride.

Example 17

The general procedure of Example 15 is repeated except that the propargyl bromide utilized therein is replaced by an equimolar amount of allyl bromide,
3,3-dimethylallyl bromide,
ethyl bromide,
n-propyl bromide,
isopropyl bromide,
n-butyl bromide,
isobutyl bromide,
n-amyl bromide,
isoamyl bromide,
tert-amyl bromide and
n-hexyl bromide, respectively, and there is thereby produced d,l-3-hydroxy-7-oxo-N-allylmorphinan,
d,l-3-hydroxy-7-oxo-N-(3,3-dimethylallyl)morphinan,
d,l-3-hydroxy-7-oxo-N-ethylmorphinan,
d,l-3-hydroxy-7-oxo-N-(n-propyl)morphinan,
d,l-3-hydroxy-7-oxo-N-isopropylmorphinan,
d,l-3-hydroxy-7-oxo-N-(n-butyl)morphinan,
d,l-3-hydroxy-7-oxo-N-isobutylmorphinan,
d,l-3-hydroxy-7-oxo-N-(n-amyl)morphinan,
d,l-3-hydroxy-7-oxo-N-isoamylmorphinan,
d,l-3-hydroxy-7-oxo-N-(tert-amyl)morphinan and
d,l-3-hydroxy-7-oxo-N-(n-hexyl)morphinan, respectively.

Example 18

The general procedure of Example 16 is repeated except that the propargyl bromide utilized therein is replaced by an equimolar amount of allyl bromide, 3,3-dimethylallyl bromide,
ethyl bromide,
n-propyl bromide,
isopropyl bromide,
n-butyl bromide,
isobutyl bromide,
n-amyl bromide,
isoamyl bromide,
tert-amyl bromide and
n-hexyl bromide, respectively, and there is thereby produced d,l-3-hydroxy-7-oxo-N-allylisomorphinan,
d,l-3-hydroxy-7-oxo-N-(3,3-dimethylallyl)isomorphinan,
d,l-3-hydroxy-7-oxo-N-ethylisomorphinan,
d,l-3-hydroxy-7-oxo-N-(n-propyl)isomorphinan,
d,l-3-hydroxy-7-oxo-N-isopropylisomorphinan,
d,l-3-hydroxy-7-oxo-N-(n-butyl)isomorphinan,
d,l-3-hydroxy-7-oxo-N-isobutylisomorphinan,
d,l-3-hydroxy-7-oxo-N-(n-amyl)isomorphinan,
d,l-3-hydroxy-7-oxo-N-isoamylisomorphinan,
d,l-3-hydroxy-7-oxo-N-(tert-amyl)isomorphinan and
d,l-3-hydroxy-7-oxo-N-(n-hexyl)isomorphinan, respectively.

Example 19

The general procedure of Example 9 is repeated except that the cyclopropane carboxylic acid chloride utilized therein is replaced by an equimolar amount of acetyl chloride,
propionyl chloride,
butyryl chloride,
isobutyryl chloride,
valeryl chloride,
pivaloyl chloride,
caproyl chloride,
4-methylvaleryl chloride and
2-ethylbutyryl chloride, respectively, and there is thereby produced d,l-3-hydroxy-7-oxo-N-ethylmorphinan,
d,l-3-hydroxy-7-oxo-N-(n-propyl)morphinan,
d,l-3-hydroxy-7-oxo-N-(n-butyl)morphinan,
d,l-3-hydroxy-7-oxo-N-isobutylmorphinan,
d,l-3-hydroxy-7-oxo-N-(n-amyl)morphinan,
d,l-3-hydroxy-7-oxo-N-(2,2-dimethylpropyl)morphinan,
d,l-3-hydroxy-7-oxo-N-(n-hexyl)morphinan,
d,l-3-hydroxy-7-oxo-N-(4-methylpentyl)morphinan and
d,l-3-hydroxy-7-oxo-N-(2-ethylbutyl)morphinan, respectively.

Example 20

The general procedure of Example 10 is repeated except that the cyclopropane carboxylic acid chloride utilized therein is replaced by an equimolar amount of acetyl chloride,
propionyl chloride,
butyryl chloride,
isobutyryl chloride,
valeryl chloride,
pivaloyl chloride,
caproyl chloride,
4-methylvaleryl chloride and
2-ethylbutyryl chloride, respectively, and there is thereby produced d,l-3-hydroxy-7-oxo-N-ethylisomorphinan,
d,l-3-hydroxy-7-oxo-N-(n-propyl)isomorphinan,
d,l-3-hydroxy-7-oxo-N-(n-butyl)isomorphinan,
d,l-3-hydroxy-7-oxo-N-isobutylisomorphinan,
d,l-3-hydroxy-7-oxo-N-(n-amyl)isomorphinan,
d,l-3-hydroxy-7-oxo-N-(2,2-dimethylpropyl)isomorphinan,
d,l-3-hydroxy-7-oxo-N-(n-hexyl)isomorphinan,
d,l-3-hydroxy-7-oxo-N-(4-methylpentyl)isomorphinan and
d,l-3-hydroxy-7-oxo-N-(2-ethylbutyl)isomorphinan, respectively.

We claim:
1. A compound of the formula

I wherein $R^1$ is hydrogen, (lower)alkyl, cyclopropylmethyl, cyclobutylmethyl, propargyl, allyl or 3,3-dimethylallyl, or a nontoxic pharmaceutically acceptable acid addition salt thereof.

2. A compound of claim 1 wherein $R^1$ is hydrogen, (lower)alkyl, cyclopropylmethyl or cyclobutylmethyl.

3. A 3-hydroxy-7-oxomorphinan of the formula wherein $R^1$ is hydrogen or (lower)alkyl, or a nontoxic pharmaceutically acceptable acid addition salt thereof.

4. The compound of claim 3 which is d,l-3-hydroxy-7-oxo-N-methylmorphinan, or a nontoxic pharmaceutically acceptable acid addition salt thereof.

5. The compound of claim 3 which is l-3-hydroxy-7-oxo-N-methylmorphinan, or a nontoxic pharmaceutically acceptable acid addition salt thereof.

6. The compound of claim 3 which is d,l-3-hydroxy-7-oxomorphinan, or an acid addition salt thereof.

7. The compound of claim 3 which is l-3-hydroxy-7-oxomorphinan, or an acid addition salt thereof.

8. A 3-hydroxy-7-oxoisomorphinan of the formula wherein R¹ is hydrogen or (lower)alkyl, or a nontoxic pharmaceutically acceptable acid addition salt thereof.

9. The compound of claim 8 which is d,l-3-hydroxy-7-oxo-N-methylisomorphinan, or a nontoxic pharmaceutically acceptable acid addition salt thereof.

10. The compound of claim 8 which is l-3-hydroxy-7-oxo-N-methylisomorphinan, or a nontoxic pharmaceutically acceptable acid addition salt thereof.

11. The compound of claim 8 which is d,l-3-hydroxy-7-oxoisomorphinan, or an acid addition salt thereof.

12. The compound of claim 8 which is l-3-hydroxy-7-oxoisomorphinan, or an acid addition salt thereof.

* * * * *

UNITED STATES PATENT AND TRADEMARK OFFICE
CERTIFICATE OF CORRECTION

PATENT NO. : 4,277,605
DATED : July 7, 1981
INVENTOR(S) : Joseph P. Buyniski et al.

It is certified that error appears in the above—identified patent and that said Letters Patent is hereby corrected as shown below:

The structure appearing in Claim 3 should read as follows:

Signed and Sealed this

Twenty-second Day of September 1981

[SEAL]

Attest:

Attesting Officer

GERALD J. MOSSINGHOFF

Commissioner of Patents and Trademarks